United States Patent [19]

Sentell et al.

[11] 4,336,801
[45] Jun. 29, 1982

[54] DOUCHE NOZZLE

[76] Inventors: Samuel W. Sentell, Rte. 7, Box 50;
Jean S. Mendenhall, 579 N.
Marlbourough Cir., both of
Shreveport, La. 71106; Sallie S.
Roberts, P.O. Box 80155, Baton
Rouge, La. 70808; C. Sherburne
Sentell, Jr., Box 752, Minden, La.
71055

[21] Appl. No.: 174,833

[22] Filed: Aug. 4, 1980

[51] Int. Cl.³ .............................................. A61M 3/00
[52] U.S. Cl. .................................. 128/239; 128/251
[58] Field of Search ............... 128/239, 240, 241, 245,
128/251, 248, 227, 341

[56] References Cited

U.S. PATENT DOCUMENTS

| 471,514 | 3/1892 | Reutter | 128/227 X |
| 701,124 | 5/1902 | Allen | 128/241 |
| 805,826 | 11/1905 | Vidaver | 128/241 |
| 1,535,756 | 4/1925 | Austin | 128/240 |
| 2,617,417 | 11/1952 | Condit | 128/245 |
| 2,631,586 | 3/1953 | Reilly | 128/341 X |

Primary Examiner—John D. Yasko

[57] ABSTRACT

A douche nozzle for expanding the vaginal canal and contacting the walls of the canal with either a slightly acidic or basic solution before sperm injection and during ovulation for the purpose of increasing the likelihood of selectively conceiving either a female or male baby. A process for selectively conceiving a male or female baby by injecting the appropriate solution into the vaginal canal using the douche nozzle of this invention.

9 Claims, 5 Drawing Figures

DOUCHE NOZZLE

BACKGROUND OF THE INVENTION

1. Field of the Invention

This invention relates to douche nozzles for injecting fluids into the female vaginal canal, and more particularly, to a douche nozzle having a specially designed shape, including an enlargement for blocking and dilating the vaginal canal and introducing either a slightly acidic or basic fluid in the canal to coat the canal prior to introduction of sperm into the canal to selectively increase the liklihood of conceiving either a female or male baby.

The question of sex determination of babies prior to conception has excited the curiosity of many persons both in and out of the medical profession over the years. Many techniques for achieving selective conception of a boy or girl baby have been advanced, most of which have proved to be of doubtful reliability. It has been reported in scientific literature that the sex of a baby can be predetermined at, or for as long as a few hours before conception, by inserting slightly basic and acidic solutions into the vaginal canal prior to injection of the sperm. For example, it is known that injection of an alkaline solution into the vaginal canal at or prior to ovulation and fertilization favors conception of a male child. Conversely, use of a slightly acidic douche under the same circumstances favors conception of a female baby. This selectivity in conception occurs since the movement of gynosperm containing the XX or female chromosones in the vaginal canal is inhibited by the presence of a basic or alkaline material, while movement of the androsperm containing the XY or male chromosones is inhibited by the presence of an acidic condition in the canal. Accordingly, it has been found that use of a weak bicarbonate of soda solution douche at or near ovulation greatly favors conception of a male child, while injection of a weak vinegar solution into the vaginal canal favors conception of a female baby.

It has been found that the vehicle or device for effecting insertion of the acidic or basic solution is of primary importance in effecting the desired choice of sex. While conventional douche nozzles may on occasion facilitate the desired choice, the configuration and design of the nozzle used must be carefully considered in order to maximize the chance of success in the procedure.

2. Description of the Prior Art

Many douche nozzles and vaginal syringes for effecting feminine hygiene are well known in the prior art. U.S. Pat. No. 2,888,925 to B. M. Philips is typical of these devices, and discloses a vaginal syringe apparatus which is shaped to block the vaginal canal during use, and to selectively permit fluid to flow into and out of the canal by means of a nozzle and a finger-operated nipple, respectively. The device is connected to a bag containing douche solution, and is fed by gravity, in conventional fashion.

Another device styled "Means for Facilitating Internal Flushing of Syringing" is described in U.S. Pat. No. 766,069 to J. D. Sourwine. The syringing device includes a shaped nozzle for injecting fluids into the vaginal canal during the douching operation.

As heretofore described, a key factor in effecting choice of sex during conception has been found to be the introduction of either a basic or an acidic douche solution into the vaginal canal during ovulation in such a manner as to block the canal, and subsequently coat the canal to effect contact between the solution and sperm subsequently entering the canal. Since the walls of the female vaginal canal are wrinkled and undulate, the device used to effect insertion of the fluid of choice must stretch the vaginal canal wall to smooth the wrinkles, block the canal at the correct point, and facilitate the introduction of fluid in a manner designed to thoroughly coat the vaginal canal walls.

Accordingly, it is an object of this invention to provide a new and improved douche nozzle having a round base which tapers to a round, slender neck and subsequently expands to a bulbous enlargement having multiple openings, and again tapers symmetrically to a discharge opening.

Another object of the invention is to provide a new and improved douche nozzle for insertion in, blocking and stretching the vaginal canal during ovulation and at or near conception, and introducing a quantity of acidic or basic douche fluid into the vaginal canal to thoroughly coat the walls thereof and selectively enhance the liklihood of conception of a female or male baby.

Yet another object of this invention is to provide a hollow douche nozzle device having a round base which is flat on one side and tapers to a slender, round neck on the other side, and subsequently flares to define a bulbous enlargement having multiple apertures communicating with the hollow interior of the device, and further comprising a tapering funnel extending from the enlargement to an opening in the end of the device opposite the round base, which opening and apertures are sized to facilitate a larger volume of flow through the opening than through the apertures.

A still further object of the invention is to provide a hollow douche nozzle for use in selecting the sex of a child, which nozzle is characterized by a generally round base flat on one side, and provided with a check valve and opening extending into the hollow interior, the opposite side of the base tapering to a narrow neck which flares to define a bulbous enlargement having multiple openings communicating with the hollow interior of the nozzle, and the bulbous enlargement further tapering to define an opening in the extended end of the nozzle.

Yet another object of this invention is to provide a specially designed douche nozzle for use in determining the sex of a baby during ovulation and at or prior to conception, and a process for selectively introducing either a basic or an acidic solution into the female vaginal canal by means of the douche nozzle to coat the canal lining and increase the liklihood of conception of a male or female child.

SUMMARY OF THE INVENTION

A douche nozzle designed to stretch and block the female vaginal canal, and a process for using the douche nozzle to selectively introduce a fluid having a PH of greater than 7 or less than 7 into the vaginal canal during ovulation and at or near the time of conception for the purpose of increasing the liklihood of conceiving a boy or a girl baby, which nozzle is hollow and is characterized by a generally round base having a flat surface on one side, a ball check and opening mounted on the flat surface of the base, with the opening extending through the base and communicating with the hollow interior of the nozzle, and a nipple spaced from the ball check and having a like opening, the opposite side of the nozzle base tapering opposite the flat surface to define a narrow, round neck, and shaped to form a bulbous plug or enlargement having multiple openings communicating with the hollow interior of the nozzle, the enlargement then tapering to a central opening in the nozzle at a point spaced from and opposite the ball check opening. A tube connects the ball check opening with a conventional bag designed to contain a quantity of douche solution.

BRIEF DESCRIPTION OF THE DRAWING

The invention will be better understood by reference to the accompanying drawing, wherein.

DESCRIPTION OF THE PREFERRED EMBODIMENTS

Figure 1:
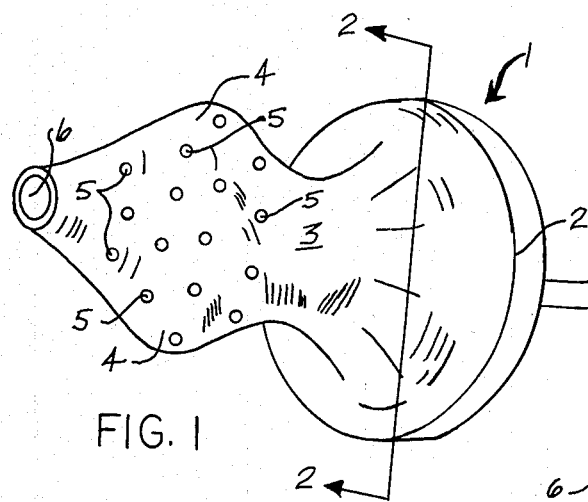
FIG. 1 is a perspective view of the douche nozzle of this invention.
Figure 5:
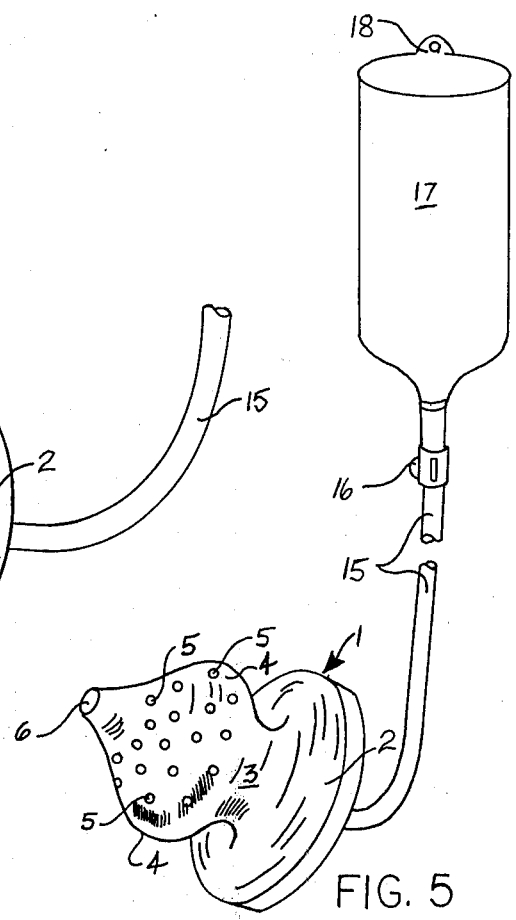
FIG. 5 is a perspective view of the nozzle illustrated in FIG. 1 in functional position attached to a bag containing douche solution.
Figure 2:
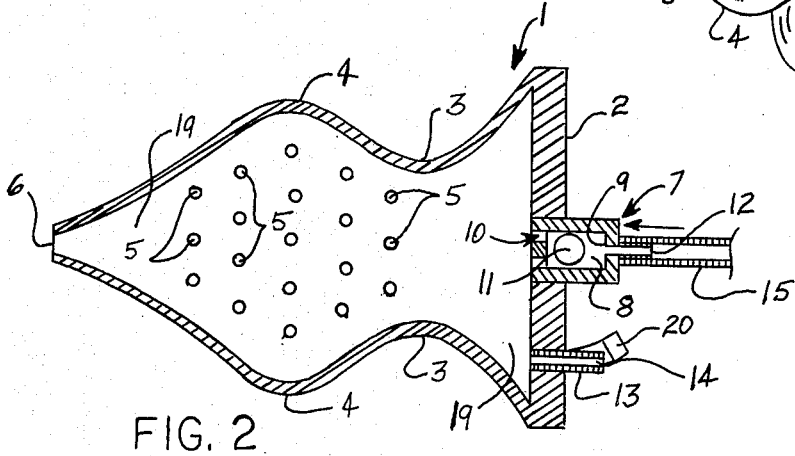
FIG. 2 is a sectional view, taken along lines 2—2 of the nozzle illustrated in FIG. 1.
Figure 3:
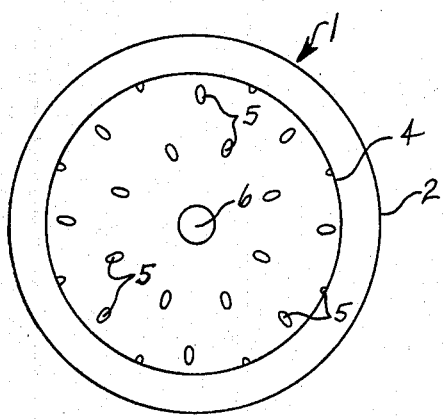
FIG. 3 is a front elevation of the nozzle illustrated in FIG. 1.

Referring to FIGS. 1, 3 and 5 of the drawing the douche nozzle of this invention is generally illustrated by reference numeral 1, and is hollow and shaped to define a generally round nozzle base 2, which is flat on one side and tapers on the opposite side to form a narrow, round and symmetrical neck 3. The neck 3 is further tapered outwardly to define a round, bulbous enlargement 4, having a plurality of enlargement apertures 5, which extend through the wall of douche nozzle 1 to communicate with the hollow interior 19, illustrated in FIG. 2. The enlargement 4 is then tapered forwardly of the neck 3 to further define a nozzle aperture 6 in the extreme end of douche nozzle 1, spaced from nozzle base 2. As illustrated in FIG. 5 of the drawing, a length of tubing 15 connects douche nozzle 1 with a conventional bag 17, which is designed to contain douche solution and feed the solution by gravity through tubing 15 and into douche nozzle 1. Bag 17 is fitted with a bag tab 18 for suspending the bag at a level above the douche nozzle 1, and a clip 16 serves to regulate the flow of douche solution from bag 17 into douche nozzle 1.

Figure 4:
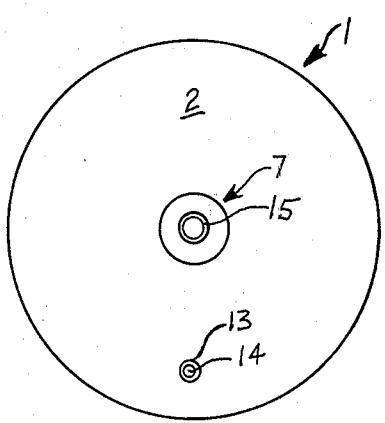
FIG. 4 is a rear elevation of the nozzle.

Referring now to FIGS. 2 and 4 of the drawing, in a preferred embodiment of the invention a ball check, generally illustrated by reference numeral 7, is provided in the center of nozzle base 2, and defines a ball chamber 8, fitted with a ball seat 9 at the upstream end of the chamber to facilitate sealing of ball check nipple 12 by ball 11 if fluid should reverse its flow from the normal direction of flow into douche nozzle 1 indicated by the arrow. A ball cage 10 is fitted to the opposite, or downstream end of ball chamber 8 to permit unobstructed flow of douche fluid through ball chamber 8 and into the hollow interior 19 of douche nozzle 1. A nozzle base nipple 13 is also provided in nozzle base 2, with the nipple aperture 14 communicating with hollow interior 19 of douche nozzle 1, and a nipple cap 20 secured to nozzle base nipple 13 and designed to removably cover the end of the nozzle.

It will be appreciated by those skilled in the art that the douche nozzle of this invention may be constructed from substantially any material known to those skilled in the art to form a smooth, firm outer surface. Accordingly, such materials as ceramics, hard rubber, plastic and fiberglass, in nonexclusive particular, can be used to shape the nozzle. Furthermore, the nozzle can be constructed in various sizes, although it is important that the ratio of the inside diameter of nozzle aperture 6 to the internal diameter of enlargement 4 be kept constant. For example, in a preferred embodiment of the invention, and for most applications, an acceptable inside diameter of nozzle aperture 6 is about ¼ of an inch, and the internal diameter of the nozzle enlargement 4 is about 1¾ inches. Accordingly, a preferred ratio of inside nozzle aperture diameter to the internal enlargement diameter is about 1:7. This ratio is important, since the flow of douche fluid from bag 17 into douche nozzle 1 must not only flow through nozzle aperture 6, but the fluid pressure in hollow interior 19 must be sufficiently great to force fluid uniformly through enlargement apertures 5. In a most preferred embodiment, this flow of fluid is greater through nozzle aperture 6 than through enlargement apertures 5. In another preferred embodiment of the invention, enlargement apertures 5 are about 1/16 of an inch in diameter, and from about 15 to about 40 apertures are provided in enlargement 4 on about a ⅜ inch spacing. In a most preferred embodiment of the invention the diameter of nozzle aperture 6 is ¼ of an inch; the internal diameter of nozzle enlargement 4 is about 1¾ inches; the internal diameter of neck 3 is about ¾ of an inch; the diameter of enlargement apertures 5 is about 1/16 of an inch; and 25 enlargement apertures are provided in enlargement 4.

Referring now to FIGS. 2 and 5 of the drawing, in use, the douche nozzle 1 of this invention is first attached to one end of tubing 15, which end is fitted tightly on ball check nipple 12. The opposite end of tubing 15 is attached to the bottom or drain of bag 17, and bag 17 is suitably elevated and secured above douche nozzle 1 by means of bag tab 18. Clip 16 is secured to tubing 15, and the douche apparatus is ready for use. A weak solution of either bicarbonate of soda or vinegar, depending upon the sex selection made, is then prepared by mixing four teaspoons of bicarbonate of soda to one quart of water, or four teaspoons of vinegar in one quart of water, and the solution of choice is thoroughly mixed and poured into bag 17. The douche nozzle 1 is then inserted into the vaginal canal and clip 16 is removed from tubing 15 or adjusted to allow the douche fluid to flow from the bag into hollow interior 19 of douche nozzle 1. A finger or nipple cap 20 is initially placed over the projecting end of nozzle base nipple 13 to prevent fluid from prematurely exiting douche nozzle 1 after air in the hollow interior 19 of douche nozzle 1 is expelled by displacement of the fluid. When the nozzle fills with fluid, the solution flows through nozzle aperture 6 and enlargement apertures 5 to coat the vaginal canal, and when a predetermined quantity of fluid has flowed into the vaginal canal, the finger or nipple cap 20 is removed from the end of nozzle base nipple 13 and fluid is allowed to flush from the vaginal canal and exit douche nozzle 1 by means of nipple aperture 14. Nipple cap 20 is particularly useful to free both hands of the user to squeeze bag 17 in order to increase the flow rate of the solution through douche nozzle 1, and to increase the fluid pressure inside hollow interior 19 for better distribution of fluid through enlargement apertures 5.

It will be appreciated by those skilled in the art that a very important feature of this invention is the design and configuration of the douche nozzle 1. The exterior surface configuration is shaped to first block the vaginal canal, and then coat the canal with a selected solution for contact with the sperm, which are subsequently introduced into the canal. The inner surface of the vaginal canal is stretched and exposed to the solution by action of the enlargement 4, and the fluid solution is prevented from exiting the canal by nozzle base 2. The annulus created in the vaginal canal by neck 3 serves to permit fluid to more freely flow from apertures 5.

It will be further appreciated that for best results the device should be used before the injection of sperm into the vaginal canal and near the time of ovulation and conception in order that the desired interaction between the sperm and solution may occur to achieve the desired selective conception.

Accordingly, having described my invention with the particularlity set forth above, what is claimed is:

1. A douche nozzle for discharging douche solution into the vaginal canal, having a hollow interior and comprising a base having a first surface tapering from the outer periphery of said base toward a central, longitudinal axis through the center of said base to define a narrow, round neck, said neck having a second surface continuous with said first surface and tapering away from said base and said axis to further define a bulbous enlargement spaced from said base and having a plurality of apertures communicating with said hollow interior, and said enlargement further characterized by a third surface continuous with said second surface and tapering toward said axis and away from said base to define a nozzle aperture communicating with said hollow interior, wherein the ratio of the inside diameter of said nozzle aperture to the inside diameter of said enlargement is about 1 to 7.

2. The douche nozzle of claim 1 wherein said plurality of apertures is from about 15 to about 40 apertures, and each of said apertures is about 1/16 of an inch in diameter.

3. The douche nozzle of claim 1 further comprising one-way valve means provided in said base for allowing fluid to flow into said hollow interior and preventing fluid from exiting said hollow interior through said valve means.

4. The douche nozzle of claim 1 further comprising a nipple provided in said base for allowing fluid to exit said hollow interior and flush said douche nozzle.

5. The douche nozzle of claim 1 further comprising:
   (a) one-way valve means provided in said base for allowing fluid to flow into said hollow interior and preventing fluid from exiting said hollow interior through said valve means; and
   (b) a nipple provided in said base for allowing fluid to exit said hollow interior and flush said douche nozzle.

6. A douche nozzle for distributing douche solution into the vaginal canal and having a hollow interior comprising:

(a) a smoothly rounded base having a substantially flat first side;
   (b) a first smooth, tapered surface extending inwardly toward an axis perpendicular to the plane of said base, said axis extending through the center of said base, and said surface extending from the upper periphery of said base opposite said first side to a narrow, rounded neck portion;
   (c) a second smooth, tapered surface extending from said neck portion outwardly away from said axis and said base to define a smooth, round bulbous enlargement having a plurality of apertures communicating with said hollow interior;
   (d) a third smooth, round tapered surface extending from said enlargement downwardly toward said axis and away from said base to define a distal portion;
   (e) a nozzle aperture formed in the end of said distal portion and communicating with said hollow interior, wherein the ratio of the inside diameter of said nozzle aperture to the inside diameter of said enlargement is about 1 to 7;
   (f) one-way valve means provided in said base for allowing fluid to enter said hollow interior and preventing fluid from exiting said hollow interior through said valve means; and
   (g) a nipple provided in said base for allowing fluid to exit said hollow interior and flush said douche nozzle.

7. A method for selecting the sex of a baby during ovulation and prior to conception by using a douche nozzle and douche solution comprising:
   (a) Preparing a douche solution having a selected PH;
   (b) inserting into the vaginal canal a douche nozzle further comprising: a hollow interior and a base; attachment means in cooperation with said hollow interior for connecting a length of rubber tubing to said base; a first tapered wall portion extending downwardly from said base and away from said base to define a narrow, round neck; a second tapered wall portion continuous with said first tapered wall portion extending upwardly and away from said base to define a round, bulbous enlargement having a plurality of apertures therein; and a third tapered wall portion continuous with said second tapered wall portion extending downwardly from said enlargement and away from said base to define a nozzle aperture communicating with said hollow interior, wherein the ratio of the inside diameter of said nozzle aperture to the inside diameter of said enlargement is about 1 to 7; and
   (c) introducing said solution into said tubing and said hollow interior and said douche nozzle.

8. The method of claim 7 wherein said PH is greater than 7 and said method favors conception of a male baby.

9. The method of claim 7 wherein said PH is less than 7 and said method favors conception of a female baby.

* * * * *